(12) United States Patent
Gao

(10) Patent No.: US 11,771,794 B1
(45) Date of Patent: Oct. 3, 2023

(54) AROMATHERAPY NEBULIZER

(71) Applicant: SHENZHEN SUNTEK ELECTRONIC CO., LTD., Shenzhen (CN)

(72) Inventor: Yong Gao, Shenzhen (CN)

(73) Assignee: SHENZHEN SUNTEK ELECTRONIC CO., LTD., Shenzhen (CN)

( * ) Notice: Subject to any disclaimer, the term of this patent is extended or adjusted under 35 U.S.C. 154(b) by 0 days.

(21) Appl. No.: 17/838,151

(22) Filed: Jun. 10, 2022

(30) Foreign Application Priority Data

Apr. 12, 2022 (CN) .......................... 202220839231.1

(51) Int. Cl.
| | |
|---|---|
| *B05B 7/32* | (2006.01) |
| *A61L 9/14* | (2006.01) |
| *A61L 9/013* | (2006.01) |
| *A61L 9/012* | (2006.01) |
| *B05B 7/04* | (2006.01) |

(52) U.S. Cl.
CPC ................ *A61L 9/14* (2013.01); *A61L 9/012* (2013.01); *A61L 9/013* (2013.01); *B05B 7/0483* (2013.01); *B05B 7/32* (2013.01); *A61L 2209/134* (2013.01)

(58) Field of Classification Search
CPC . A61L 9/14; A61L 9/012; A61L 9/013; A61L 2209/134; B05B 7/0483; B05B 7/32
See application file for complete search history.

(56) References Cited

U.S. PATENT DOCUMENTS

| | | | |
|---|---|---|---|
| 2010/0084484 A1* | 4/2010 | Sevy .................... | A61M 11/001 239/340 |
| 2016/0000959 A1* | 1/2016 | Sevy ......................... | A61L 9/14 422/4 |
| 2018/0028985 A1* | 2/2018 | Ansley ...................... | A61L 9/14 |
| 2021/0015956 A1* | 1/2021 | Lee ............................ | A61L 9/14 |
| 2021/0347554 A1* | 11/2021 | Lee ........................ | B05B 14/00 |

* cited by examiner

*Primary Examiner* — Qingzhang Zhou
(74) *Attorney, Agent, or Firm* — Cheng-Ju Chiang

(57) ABSTRACT

An aromatherapy nebulizer and an aroma diffuser of the same are proposed in the present invention. The aroma diffuser includes the aromatherapy nebulizer and a main body to mount the aromatherapy nebulizer. The aromatherapy nebulizer includes an atomizer; and an essential oil container. The atomizer includes an atomizing seat defined an atomization chamber therein and an outer cover defining a mist outlet. The atomizing seat is provided with an air conduit and a liquid conduit; the liquid conduit defines an essential oil channel therethrough. The essential oil channel is bent at one end of the liquid conduit which forms a liquid outlet, thereby the essential oil is absorbed upwards to the liquid conduct from the essential oil container and changes a direction sprayed out from the liquid outlet.

18 Claims, 11 Drawing Sheets

AROMATHERAPY NEBULIZER

CROSS REFERENCE TO RELATED APPLICATIONS

Figure 1:
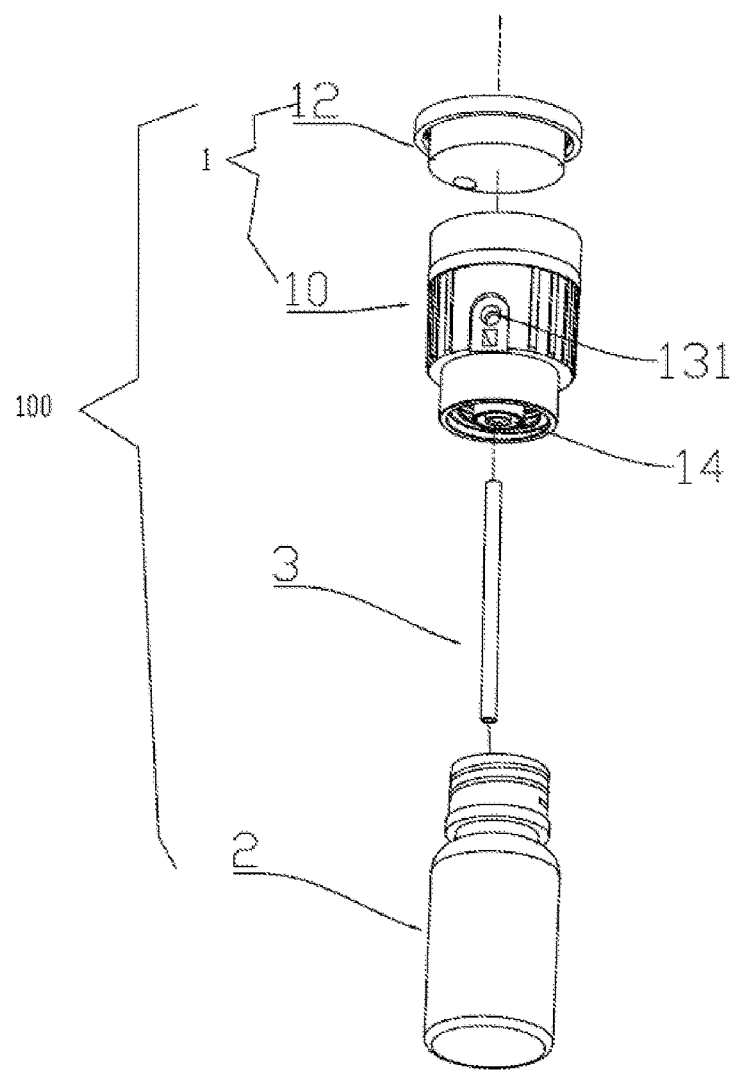
Figure 2:
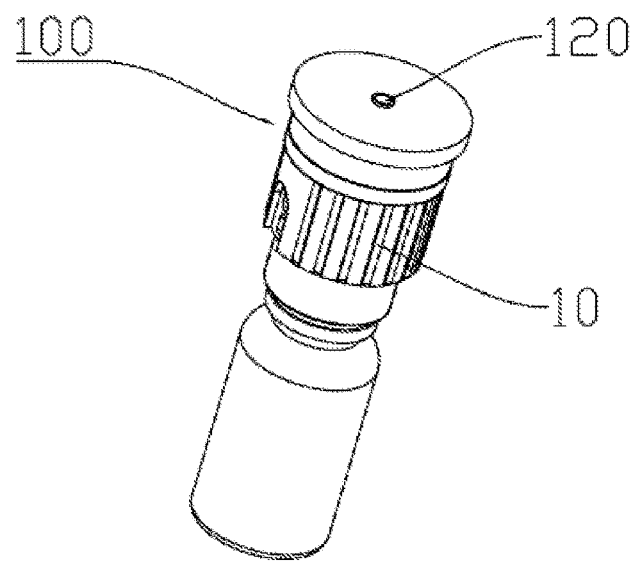

The present invention is a 35 U.S.C. § 119 benefit of earlier filing date; right of priority of Chinese Application No. 202220839231.1, filed on Apr. 12, 2022, the disclosure of which is incorporated by reference herein.

FIELD OF THE INVENTION

The present invention relates to an aroma device, and more particularly, to an aromatherapy nebulizer and an aroma diffuser of the same.

BACKGROUND OF THE INVENTION

The aroma diffuser adopts atomizer to inhale essential oil from the essential oil container to atomize the essential oil, and then diffuse into the air. The atomizer of the existing aroma diffuser is assembled by separate components, which increases the difficulty of assembly, is easy to damage, and is easy to be damaged during use. The middle parts are prone to displacement, resulting in low atomization efficiency or loss of function; and when atomizing the essential oil, the essential oil particles are uneven, the atomization effect is not good, and the atomizer is easy to wet.

SUMMARY OF THE INVENTION

A main object of the present invention is to provide an aromatherapy nebulizer, which has a hinger atomization efficiency and fine spray.

To achieve these and other objects of the present invention, an aromatherapy nebulizer is provided, comprising an atomizer and an essential oil contained. The atomizer is mounted on the essential oil container; the atomizer comprises an atomizing seat and an outer cover; an atomization chamber is formed in the atomizing seat, and a mist outlet is defined in the outer cover for communicating the atomization chamber with external environment; the atomizing seat is provided with an air conduit and a liquid conduit; the liquid conduit defines an essential oil channel therethrough for introducing the essential oil from the essential oil container into the atomization chamber; the air conduit define an air passage therethrough for introducing compressed air into the atomization chamber to atomize the essential oil and has an air outlet in the atomization chamber; the essential oil channel is bent at one end of the liquid conduit which forms a liquid outlet in the atomization chamber, whereby the essential oil is absorbed upwards in the liquid conduct from the essential oil container changes a direction sprayed out from the liquid outlet; the air outlet and the liquid outlet corporates with each other so that the air conduit blows compressed air from the air outlet towards the liquid outlet and atomize the essential oil.

In some embodiments, a bent section of the essential oil channel is: bent into a horizontal channel section relative to a vertical liquid conduit to spray the essential oil in a horizontal direction; or, bent into an inclined channel section to spray essential oil in an inclined direction; or, bent into a return channel section to spray essential oil backwards.

In some embodiments, the atomizer further comprises one connecting pipe of which one end is blocked, and the other end is connected to the liquid conduit to form a bent section of the essential oil channel, so that the essential oil in the liquid conduit enters the connecting pipe in a bent flowing direction and sprays from the liquid outlet.

In some embodiments, the end of the connecting pipe is blocked via a sealing plug; the atomization chamber has a bottom wall, the liquid conduit is arranged vertically with a top end thereof passing through the bottom wall; the connecting pipe is arranged horizontally on the bottom wall of the atomization chamber, and is connected to the liquid conduit to form the bent section of the essential oil channel that is bent from the top end of the liquid conduit, whereby the essential oil channel in the liquid conduit is bent from a vertical direction to a horizontal direction to spray the essential oil horizontally; or, the connecting pipe is inclined at a predetermined angle with respect to the bottom wall, whereby the essential oil channel is bent into an inclined direction at the top end of liquid conduit and spray essential oil in an inclined direction.

In some embodiments, the liquid conduit, the air conduit, the connecting pipe, and the atomizing seat are a whole structure formed via a plastic molding process;
one end of the connecting pipe goes through a side wall of the atomizer, and is blocked via the sealing plug.

In some embodiments, the atomizer further comprises one connecting pipe, the connecting pipe is provided with a bottom wall therein, a top end of the connecting pipe is blocked and a cavity forms in the top end of the connecting pipe; a top end of the liquid conduit extends through the bottom wall to the cavity in the connecting pipe; the connecting pipe is provided with another channel therein of which a top end extending through the bottom wall to the cavity, whereby said another channel forms a bent section of the essential oil channel and connects the liquid conduit via the cavity of the connecting pipe.

In some embodiments, the top end of the connecting pipe is blocked via a sealing plug; said another channel is parallel to the liquid conduit or is set at a preset angle with respect to the liquid conduit, whereby, the essential channel is bent backwards parallel or obliquely from the top end of the liquid conduit; the liquid conduit, the air conduit, the connecting pipe, and the atomizing seat are a whole structure formed via a plastic molding process.

In some embodiments, the atomizer further comprises one connecting pipe, one end of the connecting pipe is blocked, the other end is connected to the air conduit and forms the air outlet, whereby an air passage is bent from the air conduit to the connecting pipe to change a blowing direction of compressed air from the air outlet.

In some embodiments, the air conduit is arranged horizontally or at an inclined angel with respective to a bottom wall of the atomization chamber, and the connecting pipe is vertically arranged, whereby a horizontal or inclined air passage is bent vertically downwards to form the air outlet; the liquid conduit is connected to one horizontal or inclined connecting pipe of which one end is blocked, and the other end is connected to a top end of the liquid conduit and forms a liquid outlet, whereby the essential oil channel of the liquid conduit is bent into a horizontal or inclined section from the top of the liquid conduit, and the essential oil is sprayed in a horizontal or inclined direction; the liquid outlet is located below the air outlet; the liquid conduit, the air conduit, the connecting pipes, and the atomizing seat are a whole structure formed via a plastic molding process.

In some embodiments, a bottom surface of the outer cover is provided with a guiding channel, which is used to guide mist of atomized essential oil in the atomization chamber to the outlet to spay out, and is also used to condense droplets of the essential oil in the mist to filter and recycle large droplets of the essential oil in the mist.

In some embodiments, the bottom surface of the outer cover is fitted with an inner cover to form a cavity therein; the guiding channel is in the cavity and between the outer cover and the inner cover; the inner cover is provided with a through hole which is used for the mist in the atomization chamber to enter the cavity, and is used for droplets of the essential oil to flow back to the atomization chamber.

In some embodiments, a bottom wall of the atomization chamber is provided with a through hole communicated with the essential oil container so that the droplets of the essential oil in the atomization chamber flow back to the essential oil container; a bottom of the inner cover is tightly fitted with a top of the air conduit or liquid conduit via a support structure.

In some embodiments, an annular groove is formed on an outer wall of the atomizing seat; or the atomizing seat is sleeved with an outer shell, an annular groove is formed on an outer wall of the outer shell; one end of the air guide pipe passes through a side wall of the atomizing seat to form an air inlet in the annular groove; when the atomizer is installed to a main body of an aroma diffuser, the annular groove is closed to form an annular air chamber, and the annular air chamber connects in air flowing an air pump in the aroma diffuser with the air inlet of the air conduit.

In some embodiments, an upper end and a lower end of the annular groove on the outer wall of the atomizing seat or the outer shell are respectively provided with a sealing ring for sealing annular air chamber.

An aroma diffuser is also provided in accordance with embodiments of the present invention, comprising: an aromatherapy nebulizer; and a main body. The main body comprises a control circuit board; a battery; buttons; and an air pump electrically connected with the battery and the control circuit board, and used for generating compressed air for the aromatherapy nebulizer to atomizing essential oil. The aromatherapy nebulizer comprises an atomizer; and an essential oil container. The atomizer comprises an atomizing seat defined an atomization chamber therein; and an outer cover defining a mist outlet which is used to spray mist of atomized essential oil in the atomization chamber to external environment. The atomizing seat is provided with an air conduit and a liquid conduit; the liquid conduit defines an essential oil channel therethrough for introducing the essential oil from the essential oil container into the atomization chamber; the air conduit define an air passage therethrough for introducing compressed air into the atomization chamber to atomize the essential oil and has an air outlet in the atomization chamber; the essential oil channel is bent at one end of the liquid conduit which forms a liquid outlet, whereby the essential oil is absorbed upwards to the liquid conduct from the essential oil container and changes a direction sprayed out from the liquid outlet; the air outlet and the liquid outlet corporates with each other so that the air outlet blows compressed air towards the liquid outlet.

Advantages of the Present Invention is:

the essential oil channel is bent along the liquid conduit to change the spray direction of the essential oil, so as to reduce the blowing resistance of the air outlet and improve the atomization effect.

Other advantages and features of the present invention will be fully understood by reference to the following specification in conjunction with the accompanying drawings, in which like reference signs denote like components of structure.

BRIEF DESCRIPTION OF THE DRAWINGS

FIG. 1 is an exploded view of the aromatherapy atomizer in accordance with an embodiment of the present invention;

FIG. 2 is a perspective view of the aromatherapy nebulizer in accordance with the embodiment of the present invention;

FIG. 3 is a perspective view of the aroma diffuser in accordance with the embodiment of the present invention;

FIG. 4 is an exploded view of the aroma diffuser in accordance with the embodiment of the present invention;

FIG. 5 is a perspective view of the aroma diffuser in accordance with another embodiment of the present invention;

FIG. 6 illustrates an internal structure of the aroma diffuser in accordance with another embodiment of the present invention;

FIG. 7 is an exploded view of an atomizer in accordance with a first embodiment of the present invention.

FIG. 8 is another exploded view of the atomizer in accordance with the first embodiment of the present invention;

FIG. 9 is a horizontal sectional view of atomizer in accordance with the first embodiment of the present invention;

FIG. 10 is an axial sectional view of atomizer in accordance with of the first embodiment of the present invention;

FIG. 11 is an exploded view of atomizer in accordance with a second embodiment of the present invention;

FIG. 12 is a perspective view of the atomizer in accordance with the second embodiment of the present invention;

FIG. 13 is a horizontal sectional view of the atomizer in accordance with the second embodiment of the present invention;

FIG. 14 is an axial sectional view of the atomizer in accordance with the second embodiment of the present invention;

FIG. 15 is another axial sectional view of the atomizer in accordance with the second embodiment of the present invention;

FIG. 16 is an exploded view of the atomizer in accordance with a third embodiment of the present invention;

FIG. 17 is an axial sectional view of the atomizer in accordance with the third embodiment of the present invention;

FIG. 18 illustrates a main body of the aroma diffuser cooperating the atomizer in accordance with a fourth embodiment of the present invention;

FIG. 19 is an axial sectional view of the atomizer in accordance with a fifth embodiment of the present invention;

FIG. 20 is a perspective view of the atomizer in accordance with the fifth embodiment of the present invention; and FIG. 21 is an exploded view of the atomizer in accordance with the fifth embodiment of the present invention.

DETAILED DESCRIPTION OF THE INVENTION

The embodiments of the present invention and the features in the embodiments can be combined with each other. The following describes the present invention in further detail with reference to the drawings and specific embodiments.

Refer to FIGS. 1-6, the embodiments of the present invention disclose an aromatherapy nebulizer 100 and aroma diffuser 1000 of the same. The aromatherapy nebulizer 100 comprises an atomizer 1 and an essential oil container 2, the atomizer 1 is mounted to the essential oil container 2, and a dip tube 3 extends from the atomizer 1 into the essential oil container 2. The essential oil container 2 contains liquid essential oil, and the essential oil is absorbed into the atomizer 1 via the liquid dip tube 3 to form a mist in the atomizer 1, and then sprayed out from a mist outlet 120.

In one embodiment, an opening of the essential oil container 2 is provided with threads, the atomizer 1 is provided with inner threads, thereby, the atomizer can be threadedly connected with the opening of the essential oil container 2. The atomizer 1 comprises an atomizing seat 10 and an outer cover 12, an atomization chamber 11 is formed inside the atomization atomizing seat 10, and the outer cover 12 encloses the atomization chamber 11. The outer cover 12 is provided with a through hole communicated the atomization chamber 11 with the external environment as the mist outlet 120 for spraying the mist-like essential oil in the atomization chamber 11 to the external environment.

The outer cover 12 and the atomizing seat 10 can be independent parts; the outer cover 12 is placed on an opening of atomizing seat 10 to close the inner atomizing chamber 11 and defines the mist outlet 120 therethrough. The outer cover 12 and the atomizing seat 10 may be separable or inseparable from each other. The outer cover 12 and the atomizing seat 10 may be a whole structure by bonding, fusing, or plastic integral molding.

The outer cover 12 may be positioned at a top opening of the atomizing seat. Or, the opening of the atomizing seat 10 may be set at any suitable position of the atomizing seat.

In other embodiments, the outer cover 12 and the atomizing seat 10 may also be an integral/whole structure formed at one time via plastic molding.

The atomizing seat 10 of the atomizer 1 of the present invention is preferably a whole structure made via plastic molding process, comprises an annular side wall and a bottom wall, which is engaged on the opening of the essential oil container 2. The upper of the annular side wall and the bottom wall together enclose the atomization chamber 11 in the atomizer 1, while the lower of the annular side wall and the bottom wall are engaged with the opening of the essential oil container 2. A through hole (not shown) may be defined in the bottom wall to communicate with the essential oil container 2, so that the essential oil particles or droplets in the atomizing chamber 11 can fall back into the essential oil container 2.

The atomizing seat 10 is provided with an air conduit 13 and a liquid conduit 14. The air conduit 13 and the liquid conduit 14 can be unseparated from the atomizing seat 10 to form an integral/whole structure. The air conduit 13 is used to transport compressed air generated by an air pump to the atomizing chamber 11. The liquid conduit 14 connects the dip tube 3 or is a section of the dip tube 3, and guides the essential oil liquid sucked up by the dip tube 3 into the atomizing chamber 11.

Two opposite ends of the air conduit 13 form an air inlet 131 and an air outlet 130 respectively, the air inlet 131 is communicated with an air outlet 550 of the air pump 540, and the air outlet 130 is in the atomizing chamber 11; for example, the air outlet 130 is located at a center of the bottom wall. A through hole is formed in the annular side wall of the atomizing seat 10, which can be used as the air inlet 131. In other embodiments, the through hole of the annular side wall of the atomizing seat 10 can also be used for one end of the air conduit 13 to pass through, extend into the main body 500 of the aroma diffuser 1000 and connect the air pump 540 in air flowing.

The air outlet 130 of the air conduit 13 is located inside the atomizing chamber 11, such as at the center of the bottom wall of the atomizing chamber 11, and the air conduit 13 can be radially or horizontally arranged on the bottom wall of the atomization chamber 11, or inclined at a certain angle with respect to the bottom wall. One end of the air conduit 13 passes through the side wall of the atomization chamber, the outer port forms the air inlet 131 of the atomizer, and the other end forms the air outlet 130.

The liquid conduit 14 passes through the bottom wall of the atomizing chamber 11 with a lower end connecting the dip tube 3 and a top end forming a liquid outlet 140 in the atomizing chamber 11. The liquid outlet 140 of the liquid conduit 14 is located at one side of the air outlet 130 of the air conduit 13, and corporates with the air outlet 130 so that the air outlet 130 blows compressed gas to the liquid outlet 140 to atomize the essential oil. Under the gas pressure in the atomizing chamber 11, the mist of the atomized essential oil can be sprayed out through the mist outlet 120 in the outer cover 12 of the atomizing seat 10.

In some embodiments, an outer wall of the atomizing seat 10 can be provided with one or more positioning structures such as grooves, clips, or protrusions, with is engaged with the aroma diffuser 1000 for mounting the atomizer 1 to the main body 500. In a specific embodiment, the outer wall of the atomizing seat 10 forms parallel grooves and ribs alternately. A mounting ring 50 of the diffuser 1000 is provided with corresponding ribs and grooves. The upper end of the outer wall of the atomizing seat 10 is also provided with a flange, which is clamped and matched with the upper edge of the mounting ring 50 to support the atomizer 1.

In some embodiments, the atomizer 1 can also comprise an outer shell 15 sleeved outside the atomizing seat 10, can be tightly fitted in the atomizing seat 10, or can form a whole with the atomizing seat 10 via bonding, fusing or a plastic molding process. The outer wall of the outer shell 15 is provided with the positioning structure above such as a slot or a clip, which cooperates with the matching structure set on the aroma diffuser 1000 for mounting the atomizer 1. The upper end of the outer wall of the outer shell 15 can be provided with a flange, which is clamped and matched with the upper edge of the mounting ring 50 to support the aromatherapy nebulizer 100.

Please refer to FIGS. 3-6, the present invention provides an aroma diffuser 1000, including a main body 500 and the aromatherapy nebulizer 100 installed to the main body 500. The main body 500 can be provided with a mounting ring 50, and the atomizer 1 of the aromatherapy nebulizer 100 is inserted in the mounting ring 50, and the aromatherapy nebulizer 100 is supported by the mounting ring 50. When the aromatherapy nebulizer 100 is installed outside of the main body 500, a concave surface 511 can be formed on one side of the body 500, which is adapted to the shape of the aromatherapy nebulizer 100 and accommodates the aromatherapy nebulizer 100. The mounting ring 50 is sleeved outside the atomizing seat 10, and the atomizer 1 is pluggably supported on the mounting ring 10.

The main body 500 comprises a housing 510. An air pump 540, a control circuit board 570, an air tube 550 and a battery 590 mounted in or on the housing 510. The main body 500 is also provided with buttons 580, which is electrically connected to the control circuit board 570. The air outlet 550 of the air pump 540 can be formed by a connecting tube and is connected to the air conduit 13 of the atomizer 1 for air flowing. The air pump 540 is electrically connected to the control circuit board 570, and is controlled by the control circuit board 570. The battery 590 is electrically connected to the control circuit board 570 and the air pump 540 for power supply.

Start the air pump 540 via operating the buttons 580, the air outlet 550 of the air pump 540 is connected to the air inlet 131 of the air conduit 13 of the aromatherapy nebulizer 100, so that the compressed air produced by the air pump 540 is delivered to the atomizing chamber 11. The air is supplied to the air conduit 13 by the air pump 540, and is blown out from the air outlet 130 of the air conduit 13.

Figure 3:
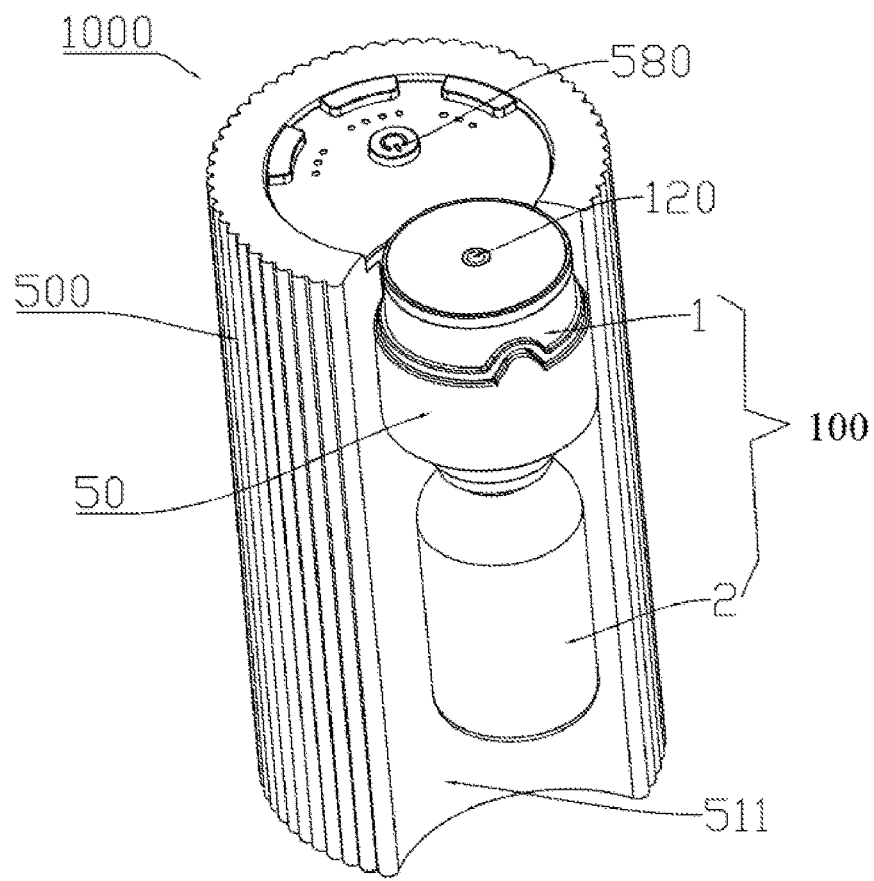
Figure 4:
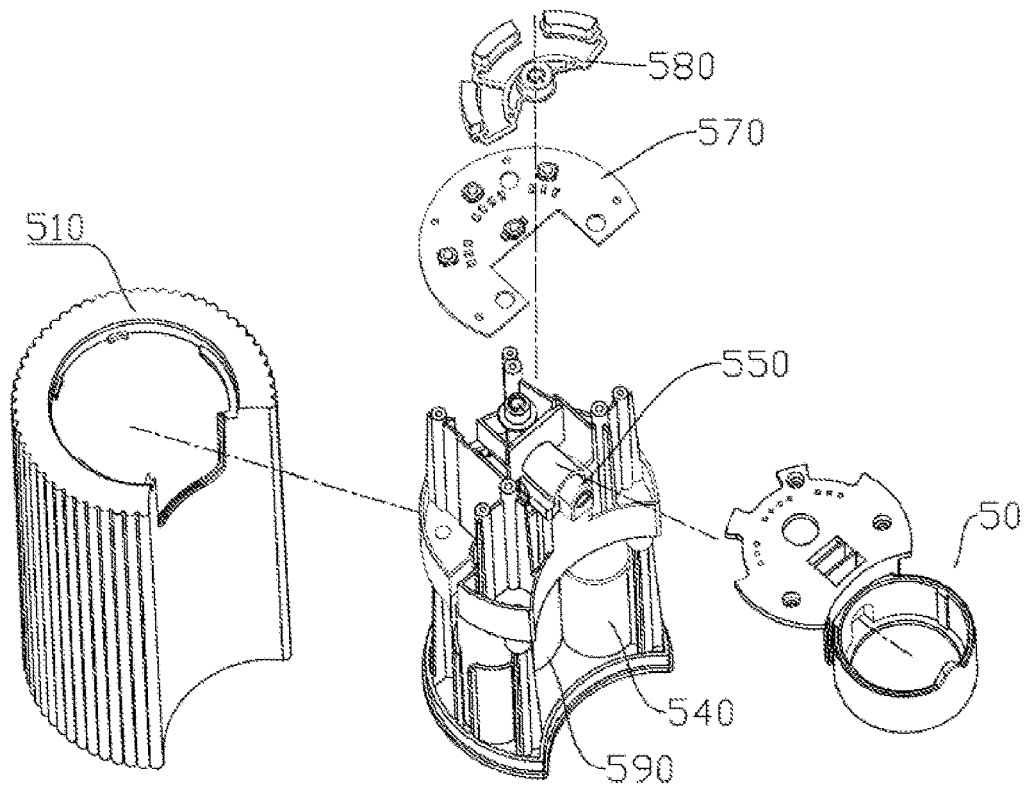
Figure 5:
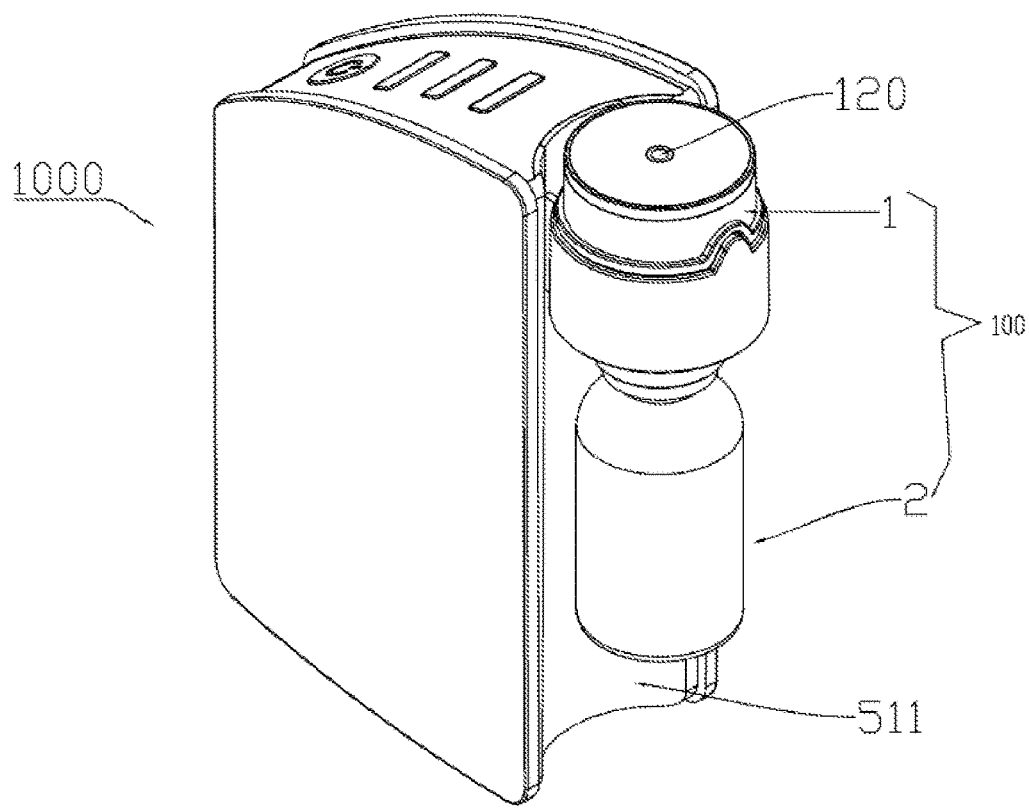
Figure 6:
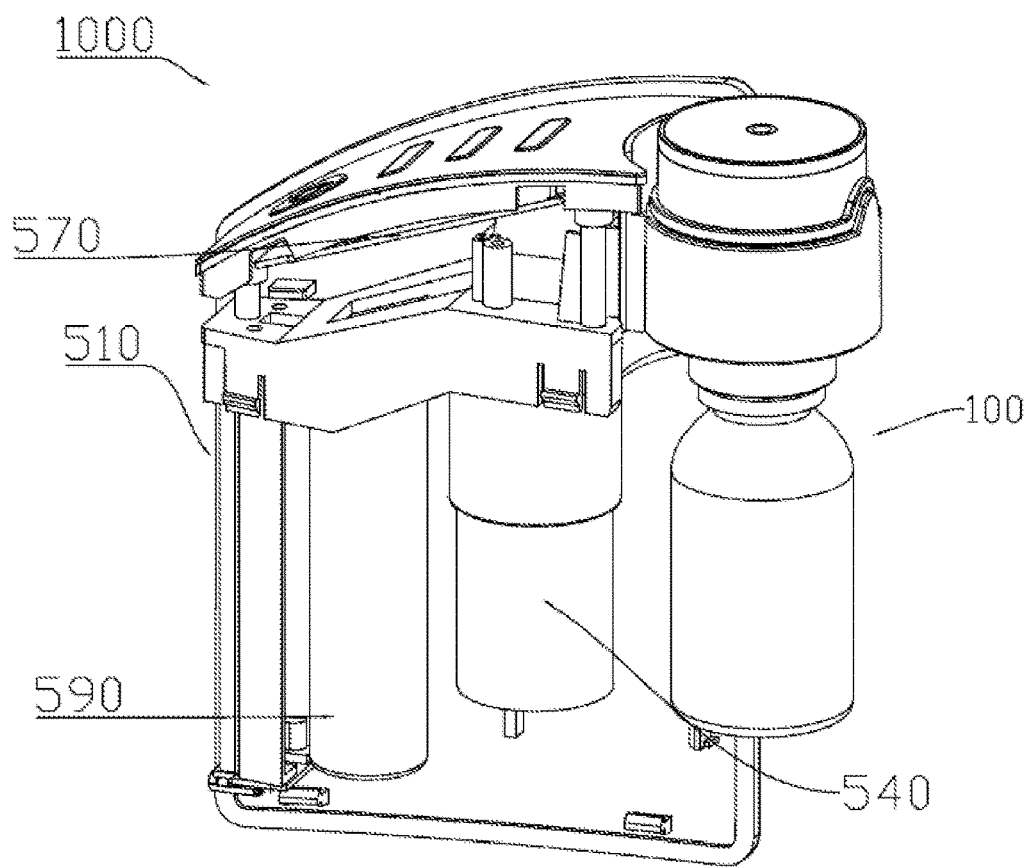
Figure 7:
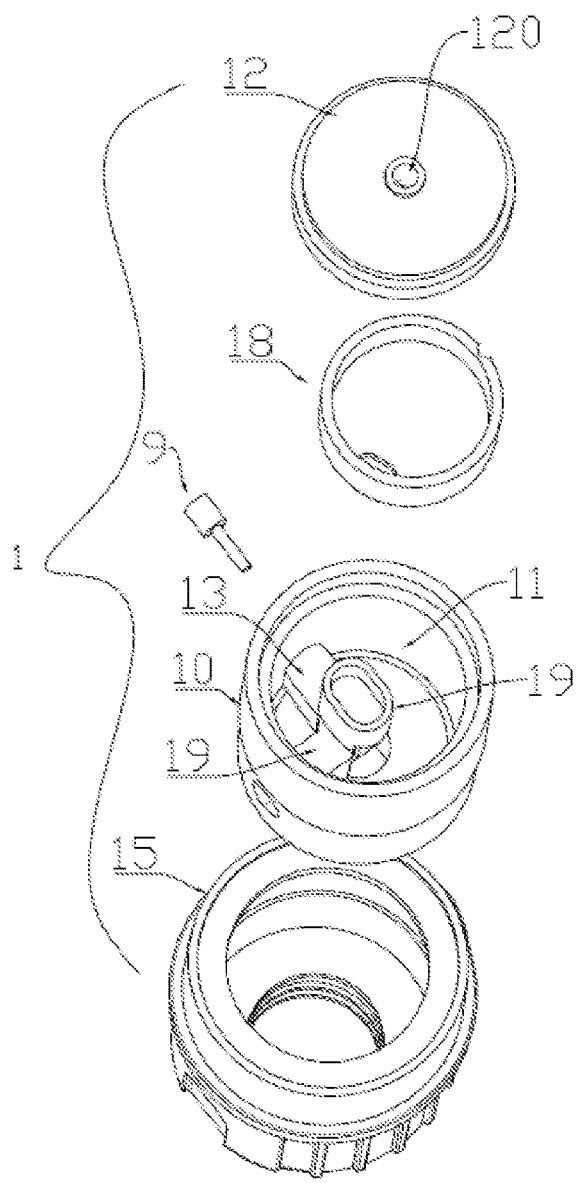
Figure 8:
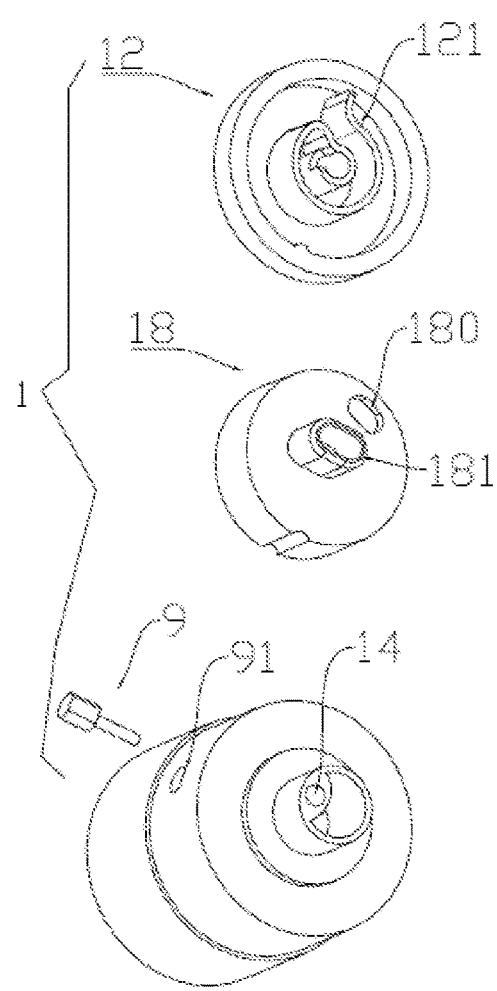
Figure 9:
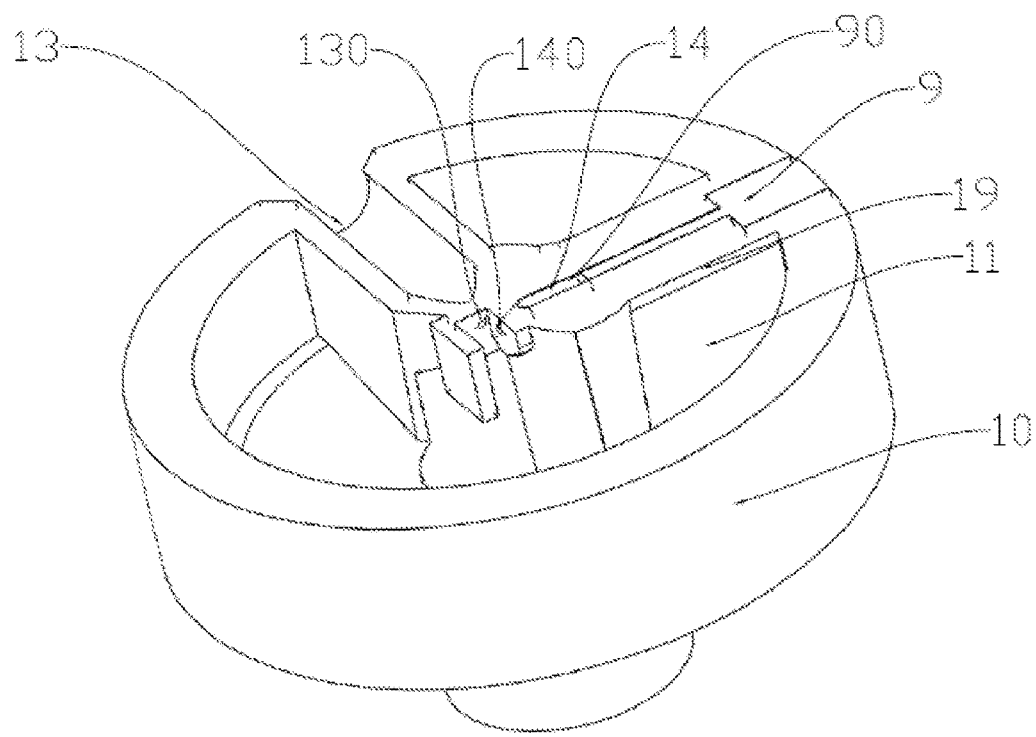
Figure 10:
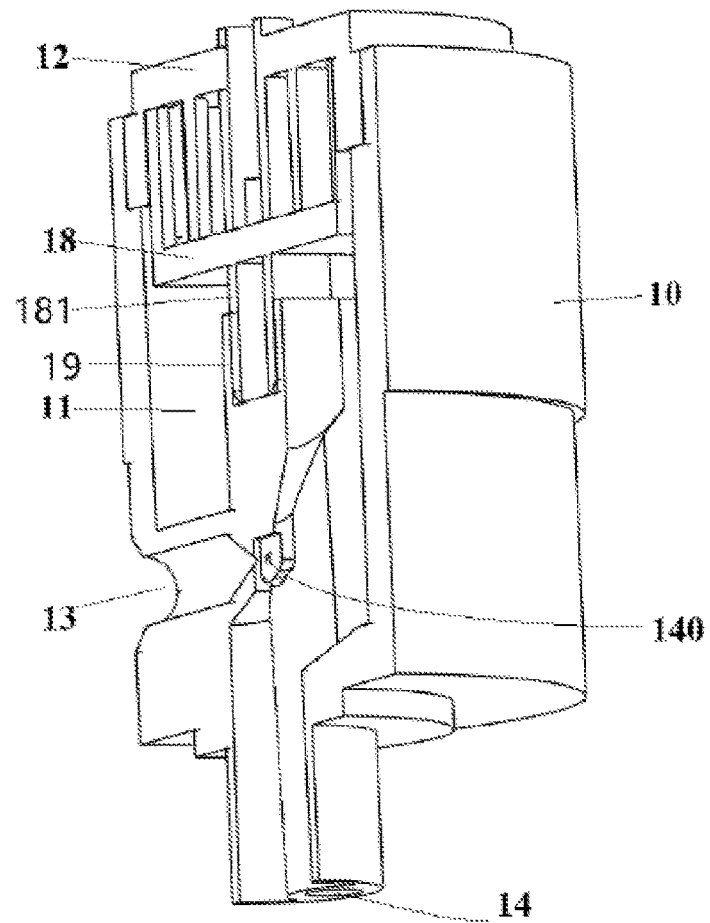
Figure 11:
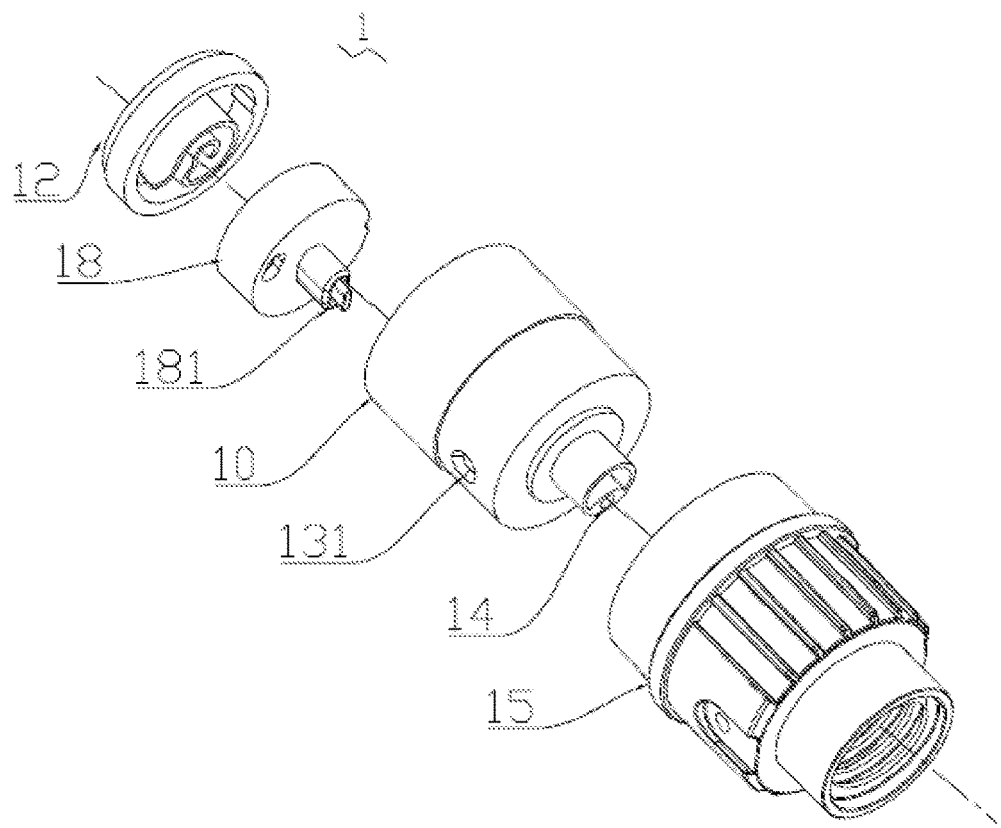
Figure 12:
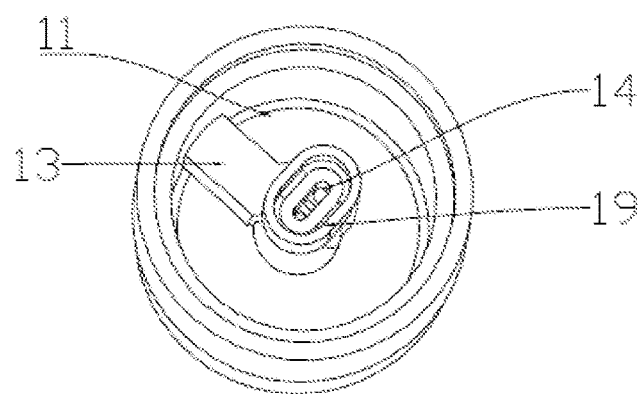
Figure 13:
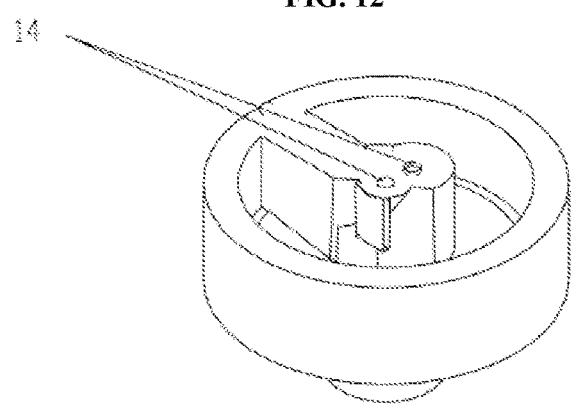
Figure 14:
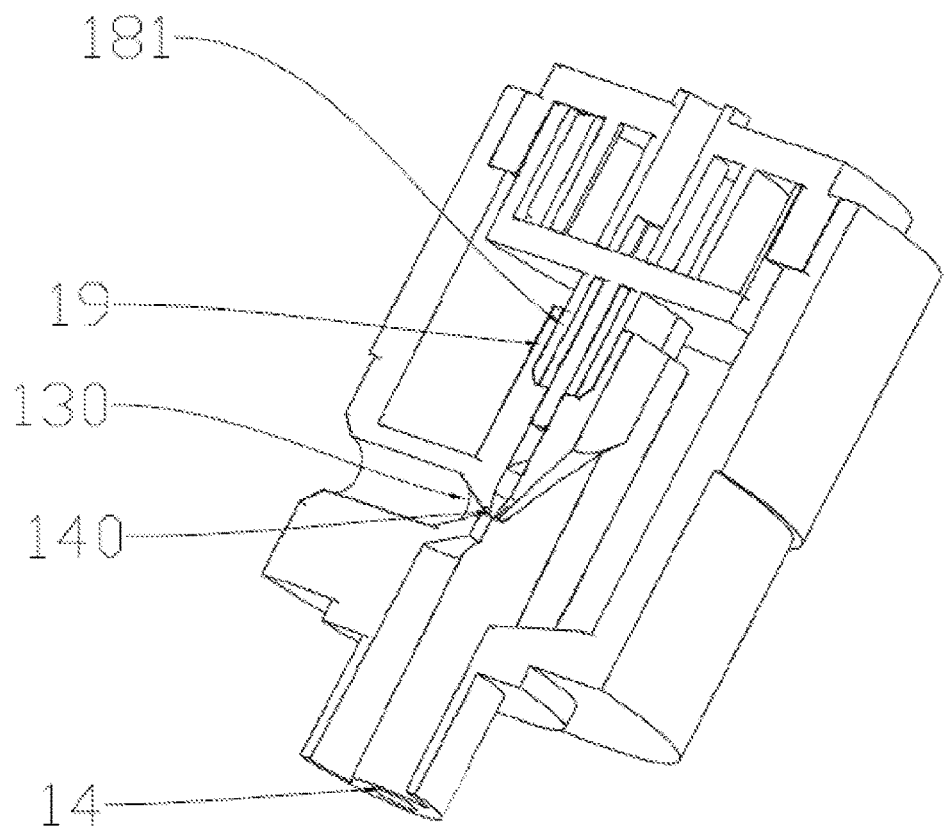
Figure 15:
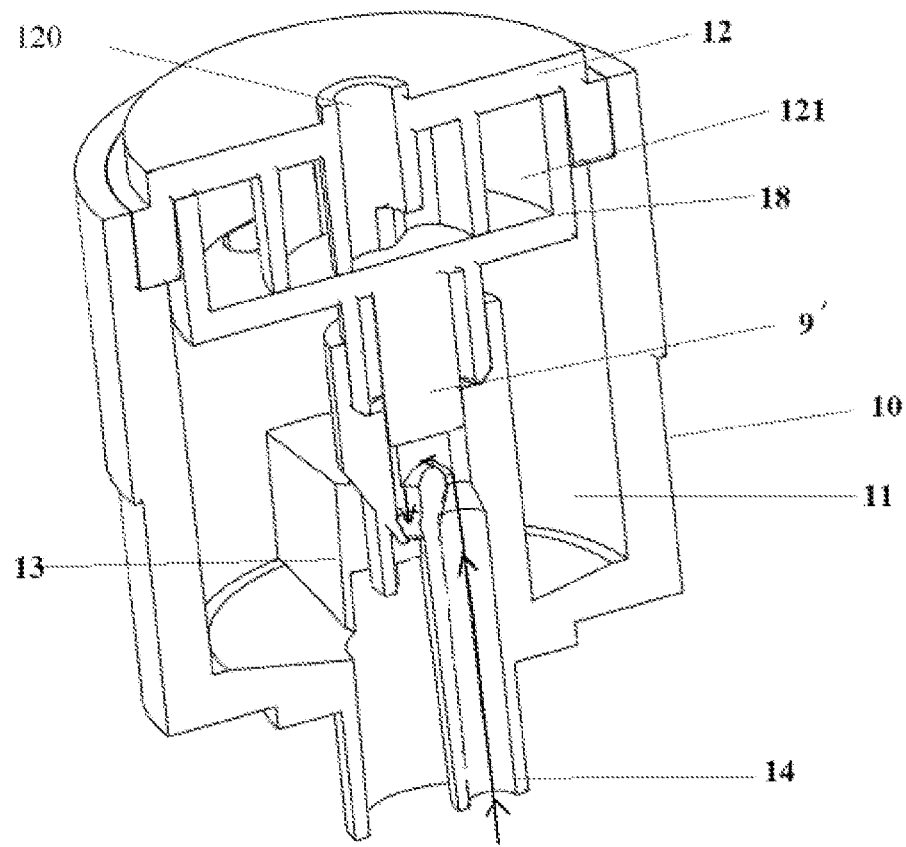

The shape of the main body 500 can be set as required, and the aroma diffuser 1000 shown in FIGS. 3-4 is a desktop device. The aroma diffuser 1000 shown in FIGS. 5-6 is a vehicle-mounted device. In the embodiments shown in FIGS. 3-6, the aromatherapy nebulizer 100 is placed outside the main body 500.

In other embodiments, the aromatherapy nebulizer 100 can also be installed inside the body 500 (namely, inside the housing 510).

Referring to FIGS. 7-21, which illustrate various embodiments of the atomizer 1, the atomizer 1 comprises an atomizing seat 10 and the outer cover 12. A guiding channel 121 can be provided on a bottom surface of the outer cover 12, and the mist of atomized essential oil in the atomizer 1 flows along the guide groove 121 to the mist outlet 120 under the air pressure, and then is sprayed out from the mist outlet 120. The guiding channel 121 is a passage for guiding the mist of atomized essential oil to flow to the mist outlet 120, large droplets of essential oil in the mist can be condensed and attached in the guiding channel 121 and will not be sprayed out from the mist outlet 120. The large droplets of essential oils can gather and flow back to the atomization chamber 11, and then flow into the essential oil container 2 from a through hole in the bottom wall of the atomization chamber 11. The guiding channel 121 is used to guide the mist of atomized essential oil in the atomizer 1 to flow to the mist outlet 120, extends the flow passage of the mist to filter large droplets of essential oil in the mist. The length and shape of the guiding channel 121 can be configured as required. Preferably, the guiding channel 121 is arranged as a curve, such as a spiral. one end of the guiding channel 121 is an inlet, and the other end is connected to the mist outlet 120. In one embodiment, the sidewalls of the guiding channel 121 protrude from the bottom surface of the outer cover 12 to a certain height. The mist of atomized essential oil flows from the inlet to the mist outlet 120 along the guiding channel 121 and is sprayed out.

In some embodiments, the atomizer 1 further comprises an inner cover 18. The inner cover 18 is fitted on the bottom surface of the outer cover 12 to enclose a cavity therein, and the guiding channel 121 is in the cavity. The edges of the outer cover 12 and the inner cover 18 may be provided with positioning structures such as snap-fit structures, or grooves/protrusions for easy installation of the inner cover 18 and the outer cover 12. The inner cover 18 may be further bonded or fused to the outer cover 12, the covers 12, 18 form a whole and fixed structure via plastic molding process. A through hole 180 is defined in the inner cover 18 and is communicated with the atomization chamber 11 and the cavity. The guiding channel 121 is in the cavity which is defined by the outer cover 12 and the inner cover 18, and mist of the atomized essential oil in the atomization chamber 11 enters the cavity from the through hole 180 of the inner cover 18, enters from the inlet of the guiding channel 121, and flows along the guiding channel 121 to the outlet 121 to spray out. Droplets of essential oil liquid in the mist can be condensed and attached to the wall of the guiding channel 121, gathered to flow back to the atomization chamber 11 through the through hole 180 in the inner cover 18, and then can flow back to the essential oil container 2 through holes in the bottom wall of the atomization chamber 11.

In some embodiments, the liquid conduit 14 can change the direction of the end (such as top end) which forms the liquid outlet 140, so that the flow direction of the essential oil is changed at the liquid outlet of the liquid conduit 14, the essential oil in the liquid conduit 14 is sprayed from the liquid outlet 140 after being bent. The liquid conduit 14 is communicated with the dip tube 3 and forms the essential oil channel of which the end with liquid outlet 140 in the atomizing chamber 11 is bent, such as bent from a length direction of the liquid conduit 14 to different directions in different shapes; for example, the end with liquid outlet 140 of the liquid conduit 14 has a backwards bending, 90-degree bending, or bending at any angle; so that the essential oil channel is bent at the end of the liquid conduit which forms the liquid outlet 140. In some embodiments, the end with the liquid outlet 140 of the liquid conduit 14 can be connected to a horizontal or inclined connecting pipe or form the bent channel section of the essential oil channel, where one end of the connecting pipe is connected to the liquid conduit 14 to form a bent section with the liquid outlet 140, and the other end is blocked with a sealing plug, so that the essential oil is sprayed in a bent direction. The bent essential oil channel makes the essential oil spray after changing the flow direction, such as obtaining a horizontal spraying, a backwards spraying, or an oblique spraying, which can reduce the resistance of air flowing from the air outlet to the sprayed essential oil at the liquid outlet 140, and can improve atomization effect. The air outlet 130 of the air conduit 13 is located at one side of the liquid outlet 14, and blows air to the liquid outlet 140.

In the atomizer 1 of the present invention, the air outlet 130 of the air conduit 13 and the liquid outlet 140 of the liquid conduit 14 are close to each other in the atomizing chamber 11, and the air outlet 130 blows compressed air toward the liquid outlet mouth 140. The air conduit 13 and/or the liquid conduit 14 can be connected to a hollow connecting pipe 19 in flow communication therebetween. Where one end of the connecting pipe 19 is sealed via a sealing plug 9, 9', the other end is connected to the air conduit 13 or the liquid conduit 14, so that an air passage of the air conduit 13 or the essential oil channel of the liquid conduit 14 change the directions or bend, and thus change the blowing direction of the air outlet 130 or spraying direction of the liquid outlet 140.

Preferably, the air conduit 13, the liquid conduit 14, the connecting pipe 19 and the atomizing seat 10 form a whole (unseparated) structure via a molding process.

Referring to FIG. 7-10, in the first embodiment, the liquid conduit 14 of the atomizer 1 has a spraying direction of the liquid outlet 140 changed. The liquid conduit 14 is vertically (along the central axis) arranged with the bottom end thereof connected with the dip tube 3 to suck the essential oil in the essential oil container 2 vertically upwards, and the top end with the liquid outlet 140 of the liquid conduit 14 in the atomization chamber 11 forms a horizontal channel section 90 via a horizontal connecting pipe 19, so that the essential oil channel is bent from the vertical direction to the horizontal direction to the liquid outlet 140 which will spray essential oil horizontally. The horizontal channel section (bent section) 90 is defined in the horizontal (radial) connecting pipe 19. An outer end of the horizontal connecting pipe 19 extends through a through hole 91 in the side wall of the atomization chamber 11, and the sealing plug 9 is inserted into the outer end of the connecting pipe 19 to block the outer end of the horizontal channel section 90. The inner end of the horizontal channel section 90 forms the liquid outlet 140. In order to facilitate the operation of the sealing plug 9 and obtain good sealing, the outer end of the horizontal channel 90 is enlarged, such as a T-shape, and correspondingly, the sealing plug 9 is also enlarged as a T-shape. The essential oil is sucked and flows upwards in the dip tube 3 and the liquid conduit 14, is bent to the horizontal channel section 90 at the top end of the liquid conduit 14, and is sprayed out from the liquid outlet 140 in a horizontal direction. The air outlet 130 of the air conduit 13 is located at the side of the liquid outlet 140, and blows compressed air towards the essential oil sprayed from the liquid outlet 140. Preferably, the blowing direction of the air outlet 130 is perpendicular to the spraying direction of liquid outlet 140. The air outlet 130 and the liquid outlet 140 corporate with each other, and one or more baffle plates can be provided on the outer edge of the air outlet 130 to make the compressed air blown out of the air outlet 130 more concentrated and effectively atomize the essential oil sprayed from the liquid outlet 140. It can be understood that the connecting pipe 19 forming the horizontal channel section 90 may be a whole (unseparated) structure with the atomizing seat 10. The liquid conduit 14, the air conduit 13, the connecting pipe 19 and the atomizing seat 10 can be formed as a whole structure via a plastic molding process, bonding, or fusing, etc.

In the present embodiment, the liquid conduit 14 comprises a vertical pipe section, has a top end thereof communicated with the horizontal (radial) connecting pipe 19 which forms a horizontally bent channel section 90, therefore, the essential oil channel in this embodiment comprises a vertical channel section and a top horizontal channel section. One end of the connecting pipe 19 extends through the side wall of the atomization chamber 11 and is blocked via the sealing plug 9; the other end forms the liquid outlet 140 and corporates with the air outlet 130 for a better atomization. The liquid outlet 140 may be in the center of the atomization chamber (not limited to the center). The connecting pipe 19 is arranged horizontally in a radial direction and are perpendicular to the vertical section of the liquid conduit 14 to form an essential oil channel with a horizontally bent section, and the liquid outlet 140 of the horizontally bent section sprays essential oil in a horizontal direction.

It can be understood that the connecting pipe 19 can be set in the atomizing chamber at an inclined angle other than horizontally, thereby the essential oil channel with a bent section at a certain angle is obtained, and the essential oil can be sucked from the essential oil container 2 and is sprayed out from the liquid outlet 140 in a bent direction at a certain angle.

Optionally, a support structure may be formed between cover assembly and the conduit assembly, so as to tightly press the inner cover to the outer cover 12, or obtain a connecting pipe to change the direction of the essential oil from the liquid outlet 140 or change the air flowing direction from the air outlet 130. Where the cover assembly comprises the outer corner 12 and the inner cover 18, and the conduit assembly comprise the air conduit 13 and the liquid conduit 14. As one embodiment, the support structure comprises a section of connecting pipe (or rod) 181 formed at the bottom surface of the inner cover 18 and a section of connecting pipe (or rod) 19 formed at the top of the air conduit 13 or the liquid conduit 14, and they are tightly sleeved or press against each other.

FIGS. 11-15 show the second embodiment in which the essential oil channel in the liquid conduit 14 is changed. The atomizer 1 comprises the outer cover 12, the inner cover 18, the atomizing seat 10 and the outer shell 15. The outer shell 15 is adapted to the shape of the atomizing seat 10, and is sleeved outside the atomizing seat 10. The outer shell 15 and the atomizing seat 10 can be a whole structure via bonding, fusing, or a plastic molding process etc.; or can be assembled with a tightening fit. The outer wall of the outer shell 15 can form a positioning structure, such as a slot/protrusion, etc., to cooperate with the aroma diffuser 1000.

The outer shell 15 or atomizing seat 10 can forms internal threads at bottom end thereof to be engaged with the opening of essential oil container 2, and forms the atomization chamber 11 therein to cover the opening of essential oil container 2, the bottom wall may define a through hole for the droplets of the essential oil liquid flowing back to the container 2.

The inner cover 18 is fastened to the bottom surface of the outer cover 12 to define the cavity inside, and the guiding channel 121 is provided in the cavity and on the bottom surface of the outer cover 12. The guiding channel 121 may form on the inner surface of the inner cover 18 in an alternative embodiment. A support structure may be formed between the cover assembly and the conduit assembly. As an example, the support structure comprises a section of connecting pipe (or rod) 181 formed at the bottom surface of the inner cover 18 and a section of connecting pipe (or rod) 19 connected to the top of the liquid conduit 14, which can abut or fit with each other. In one embodiment, a section of connecting pipe 181 formed at the bottom surface of the inner cover 18 is provided with a sealing plug 9'. The sealing plug 9' may be an integral/fixed part of the connecting pipe 181 therein or an independent part so as to seal one end of the connecting pipe 19 of which the other end is connected to the liquid conduit 14 or the air conduit 13. In other embodiment, the sealing plug 9' can be formed on the bottom surface of the inner cover 18, and the inner cover 18 is pressed against the connecting pipe 19 with the sealing plug 9' inserted in one end of the connecting pipe 19.

In one embodiment, a connecting pipe 19 is provided with a bottom wall therein, the sealing plug 9' is blocked in one end of the connecting pipe 19 so as to form a cavity in the connecting pipe 19. A top end of the liquid conduit 14 passes through a hole in the bottom wall of the connecting pipe 19 and is extended in the cavity. The connecting pipe 19 is also provided with another channel through the bottom wall thereof with a top end of the channel extending in the cavity. Therefore, one end of the liquid conduit 14 and one end of another channel are communicated in the connecting pipe 19 in the cavity; so that the essential oil channel is obtained from the liquid pipe 14 back to another channel, the other end of the channel forms the liquid outlet 140. Another channel can be set parallel to the liquid conduit 14 to form a return essential oil channel, for example, the essential oil is vertically drawn upwards in the liquid conduit 14 and then bent reversely downwards along another channel and is downwards spayed out from the liquid outlet 140, which is shown via the arrow in FIG. 15. Where the air conduit 13 can be horizontally arranged on the bottom wall of the atomizing chamber 11, and the air outlet 130 cooperates with the liquid outlet 140 so that compressed air is blown toward the liquid outlet 140 to atomize the essential oil. In this embodiment, the liquid outlet 140 is located above the air outlet 130. One or more baffle plates can be provided on the outer wall of the air outlet 130, so that the air blown out from the air outlet 130 is more concentrated to blow towards the essential oil ejected from the liquid outlet 140.

It can be understood that the connecting pipe 19 can be arranged in a vertical direction, and another channel provided in the connecting pipe 19 can be a vertical channel or an inclined direction with a certain angle deviating from the vertical direction, thereby, the essential oil channel in the liquid conduit 140 is bent back vertically or obliquely downwards in another channel, so as to spray the essential oil vertically or obliquely downwards.

The air conduit 13 can be horizontally arranged on the bottom wall of the atomization chamber 11, and can also be set at an angle with respect to the bottom wall, and the outer end of air conduit 13 passes through the through hole in the side wall of the atomizing seat, which is communicated with the air path of the air pump. The liquid conduit 14 can be vertically (along a length of the conduit 14) arranged with the top end thereof connected to a connecting pipe of which one end thereof is blocked via a sealing plug, and the other end connected to the liquid conduit 14 to form a bent essential oil channel section so as to change the flowing direction of the essential oil and the spray direction from the liquid outlet 140.

Figure 16:
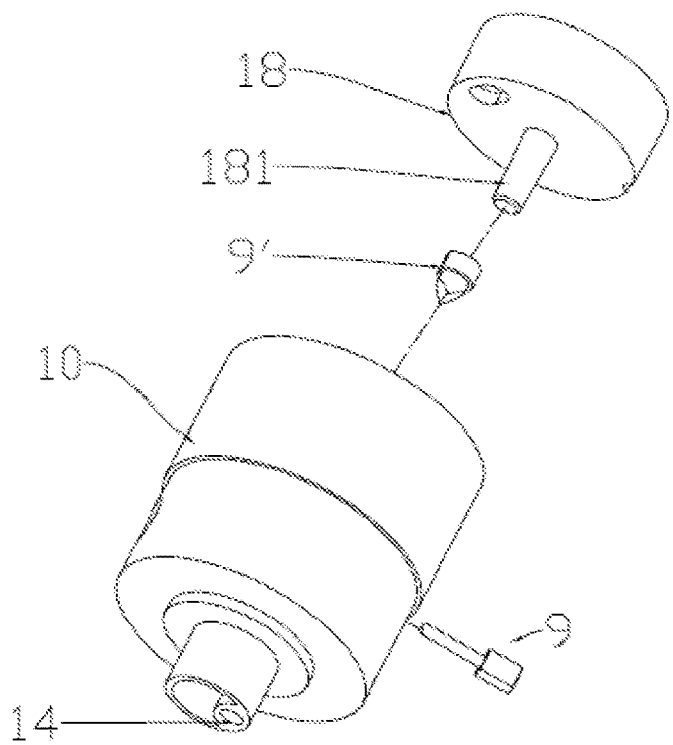
Figure 17:
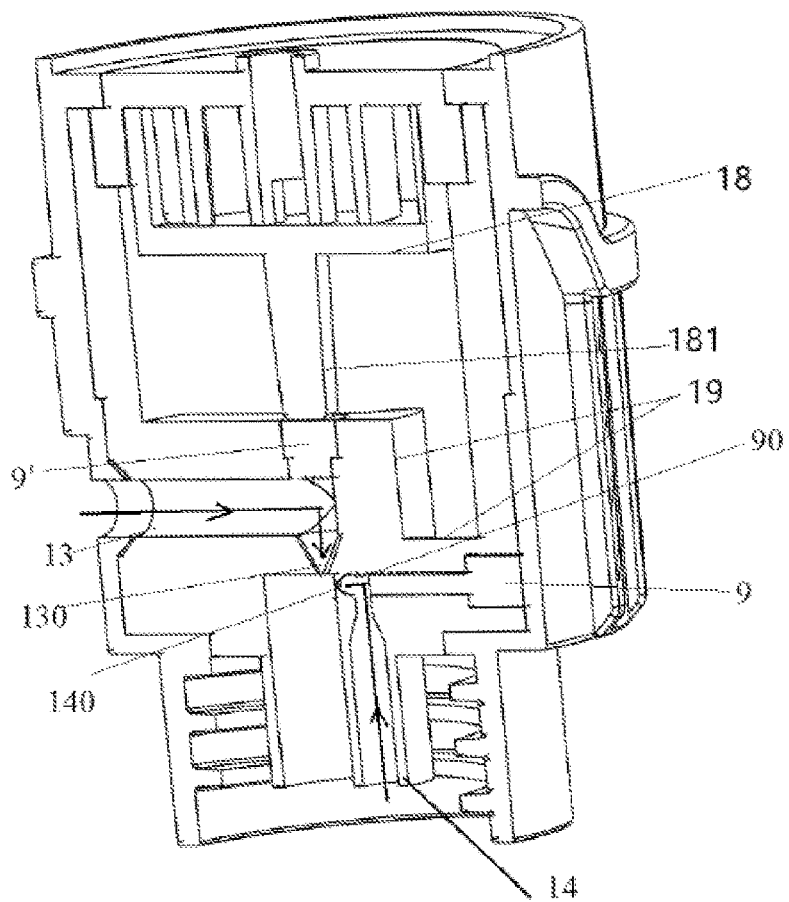

Referring to the third embodiment of the atomizer 1 as shown in FIGS. 16-17, the blowing direction of the air conduit 13 and the direction of the essential oil channel of the liquid conduit 14 are changed at the same time. The support structure 181 of the inner cover 18 is set as a rod, and a vertical connecting pipe 19 is connected to the end of the horizontal air conduit 13 which forms the air outlet 130. The vertical air passage inside the connecting pipe 19 is communicated with the air passage of the air conduit 13, and the sealing plug 9' is placed in the top of the vertical connecting 19, the bottom of the sealing plug 9' is arc-shaped, and the rod on the bottom surface of the inner cover 18 presses the sealing plug 9' downward to seal the top of the vertical connecting pipe 19, so that the air passage of the air conduit 13 is bent downward in the connecting pipe 19, the air outlet 130 is formed at the bottom end of the vertical connecting pipe 19, air flows horizontally (also can be inclined) in the air conduit 13 and is bent downwards to form a downward blowing. Another connecting pipe 19 which has a horizontal channel 90 therein is communicated with the vertical channel of the liquid conduit 14 at the top thereof, the outer end of the connecting pipe (another connecting pipe) 19 is blocked with the seal plug 9, and the other end thereof is connected to the liquid conduit 14, so that the essential oil channel in the liquid conduit 14 is bent in a horizontal direction at the top of the liquid conduit 14, and a liquid outlet 140 is formed at the other end of the connecting pipe 19, which can horizontally spray essential oil. The air outlet 130 is located above the liquid outlet 140, and the air outlet 130 blows downwards to the liquid outlet to atomize the essential oil, where the arrows in FIG. 17 indicate the flowing direction of the compressed air and the essential oil. The connecting pipe (the other connecting pipe) 19 is horizontally arranged, which may also be arranged at an inclined angel. The connecting pipe 19 connected to the air conduit 13 and the air conduit 13 can be in the same diameter direction, or at a 90-degree vertical direction or other angles. Other structures of the atomizer 1 can be the same as or similar to the above-mentioned other embodiments, and will not be repeated here.

Figure 18:
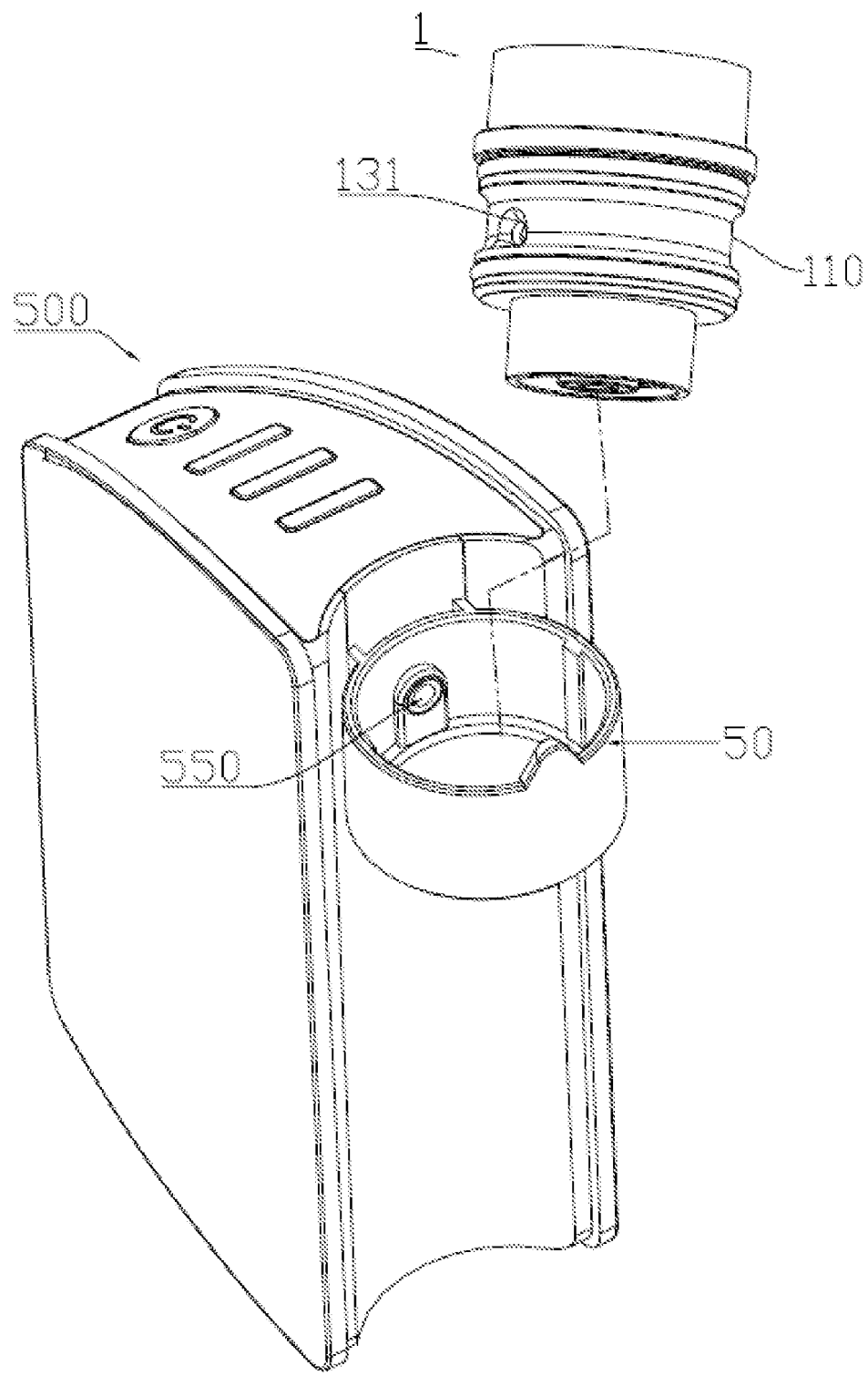

Referring to FIG. 18, in some embodiments, an annular groove 110 is formed on the outer wall of the atomizing seat 10 or the outer shell 15 of the atomizing seat 10, and the air inlet 131 of the air conduit 13 is in the annular groove 110.

When the atomizer 1 is installed in the mounting ring 50 provided on the diffuser 1000, the annular groove 110 is sealed by the mounting ring 50 to form a closed annular air chamber, the air outlet 550 of the air pump connected with the annular air chamber in air flowing, the compressed gas enters the annular air chamber, and then enters the air inlet 131 of the air conduit 13 through the annular air chamber. In this embodiment, the air inlet 131 does not need to be aligned to the air outlet 550 provided in the mounting ring, and the compressed air output by the air pump can also be input into the air guide pipe 13 via the closed annular air chamber, which is more convenient to install the atomizer to the diffuser 1000 without the need for alignment.

Figure 19:
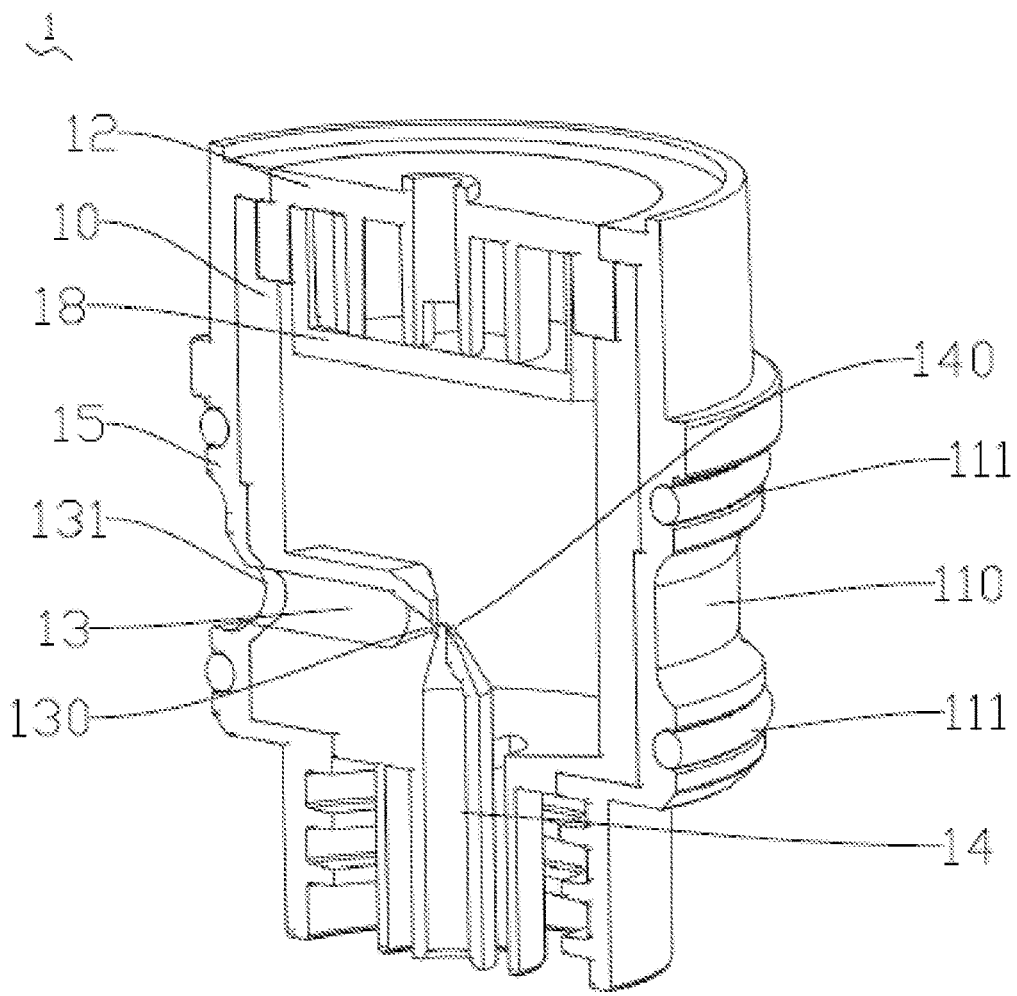
Figure 20:
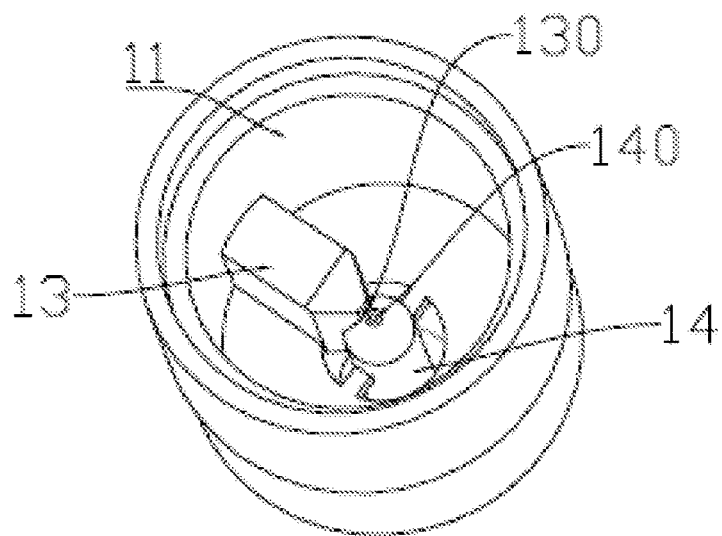
Figure 21:
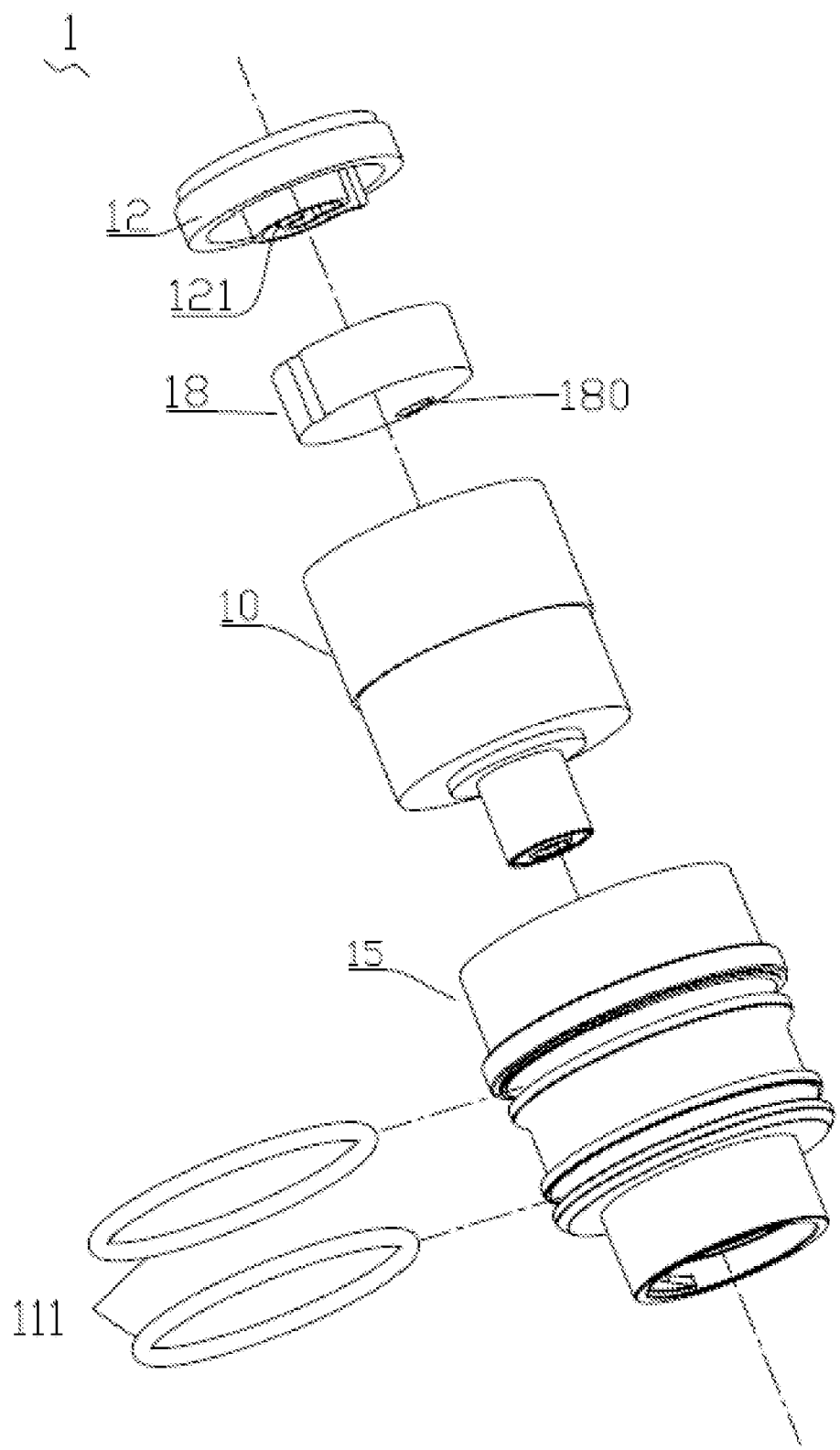

Referring to the fifth embodiment of the atomizer of the present invention shown in FIGS. 19-21, the atomizer 1 comprises an atomizing seat 10 and the outer cover 12, and the atomization chamber 11 is formed inside the atomizing seat 10. The outer cover 12 is provided with a through hole as the mist outlet 120 connecting the atomizing chamber 11 and the external environment, the bottom surface of the outer cover 12 is provided with a guiding channel 121, and mist of the atomized essential oil in the atomizer 1 flows along the guiding channel 121 to spray out. The structure and function of the guiding channel 121 are the same as or similar to the above-mentioned embodiments, and will not be repeated here.

Preferably, the atomizer 1 further comprises the inner cover 18, and the structure and function of the inner cover 18 are the same as or similar to those of the above-mentioned embodiment, and will not be repeated here.

In this embodiment, the liquid conduit 14 is vertically arranged along the axial direction of the atomizing seat 10 (or the essential oil container 2), the top of which passes through the bottom wall of the atomization chamber 11, and is in the atomization chamber 11 to form a liquid outlet 140, so as to guide the essential oil upwards into the atomizing chamber, and spray the essential oil upwards. The air conduit 13 is arranged horizontally (or inclined at a certain angle) in the atomizing chamber 11, one end of the air conduit passes through the side wall of the atomizing chamber 11. The air outlet 130 is at one side of the liquid outlet 140 to blow air to the liquid outlet laterally. In this embodiment, the air outlet 130 is located above the top of the liquid outlet 140, and air is blown vertically to the liquid outlet direction of the liquid outlet.

In this embodiment, the atomizing seat 10 and the outer shell 15 are both hollow cylinder (not limited to cylindrical shapes). The bottom end of the outer shell 15 is formed with inner threads to connect the essential oil container 2, an annular groove 110 is formed on the outer wall of the outer shell 15, and the air inlet 131 of the air conduit is in the annular groove 110 for air communication. When the atomizer 1 is installed in the mounting ring 50 provided on/in the main body 500 of the diffuser 1000, the annular groove 110 is sealed by the mounting ring 50 to form a closed annular air chamber, the air outlet of the diffuser air pump connected with the annular air chamber, the compressed gas enters the annular air chamber, and then enters the air inlet 131 of the air conduit 13 through the annular air chamber.

Further, the upper and lower ends of the annular groove 110 on the outer wall of the shell 15 or the atomizing seat 10 are respectively provided with a sealing ring 111 respectively. Preferably, the upper and lower ends of the annular groove 110 are respectively provided with an installation groove, and the sealing ring 111 is embedded in the installation groove and can be higher than the edge of the installation groove. When the sealing rings 111 are between the inner wall of the mounting ring 50 and the outer wall of the atomizing seat 10 or the outer shell 15, the annular groove 110 is sealed by the mounting ring 50 and the sealing rings 111 to form an annular air chamber. The compressed gas generated by the air pump enters the annular air chamber through the air outlet on the mounting ring 50, enters the air inlet 130 of the air conduit 13 through the annular air chamber, and is introduced into the atomization chamber 11 through the air conduit 13.

An aromatherapy nebulizer 100 provided in accordance with the embodiments of the present invention, comprises the atomizer 1 and the essential oil container 2. The essential oil container 2 and the atomizer 1 are threadedly connected, and the dip tube 3 extends from the atomizer 1 into the essential oil container 2. The essential oil container 2 contains liquid essential oil, and the essential oil is absorbed into the atomizer 1 by the dip tube 3 and the liquid conduit 14 to form a mist and then sprayed outside from the outlet (spray nozzle) 120 of the aromatherapy nebulizer 100.

The opening of the essential oil container 2 is provided with threads. The lower sidewall of the atomizer 1 is provided with internal threads, which are threadedly connected.

In the description of the present invention, it should be understood that the terms "length", "upper/top", "lower/bottom", "vertical/horizontal", "inside", "outside", etc. are based on the orientations or positional relationships shown in the accompanying drawings, which are only for the convenience of describing the present invention and simplifying the description, rather than indication or implication that the referred device or element must have a particular orientation, be constructed and operated in a particular orientation, which should not to be construed as a limitation of the invention.

Although embodiments of the present invention have been shown and described, it will be understood by those skilled in the art that various changes, modifications, and substitutions can be made in these embodiments without departing from the principle and spirit of the invention All modifications and modifications shall belong to the scope of the present invention; the protection scope of the present invention is defined by the appended claims and their equivalents.

What the invention claimed is:

1. An aromatherapy nebulizer, comprising an atomizer and an essential oil contained; wherein the atomizer is mounted on the essential oil container; the atomizer comprises an atomizing seat and an outer cover; an atomization chamber is formed in the atomizing seat, and a mist outlet is defined in the outer cover for communicating the atomization chamber with external environment; the atomizing seat is provided with an air conduit and a liquid conduit; the liquid conduit defines an essential oil channel therethrough for introducing the essential oil from the essential oil container into the atomization chamber; the air conduit defines an air passage therethrough for introducing compressed air into the atomization chamber to atomize the essential oil and has an air outlet in the atomization chamber; the essential oil channel is bent at one end of the liquid conduit which forms a liquid outlet in the atomization chamber, whereby the essential oil is absorbed upwards in the liquid conduct from the essential oil container and changes a direction sprayed out from the liquid outlet; the air outlet and the liquid outlet corporate with each other so that the air conduit blows compressed air from the air outlet towards the liquid outlet and atomizes the essential oil;

the atomizer further comprises one connecting pipe, the connecting pipe is provided with a bottom wall therein, a top end of the connecting pipe is blocked and a cavity forms in the top end of the connecting pipe; a top end of the liquid conduit extends through the bottom wall to the cavity in the connecting pipe; the connecting pipe is provided with another channel therein of which a top end extending through the bottom wall to the cavity, whereby said another channel forms a bent section of the essential oil channel and connects the liquid conduit via the cavity of the connecting pipe.

2. The aromatherapy nebulizer of claim 1, wherein a bent section of the essential oil channel is:
bent into a return channel section to spray essential oil backwards.

3. The aromatherapy nebulizer of claim 1, wherein the atomizer further comprises one connecting pipe of which one end is blocked, and the other end is connected to the liquid conduit to form a bent section of the essential oil channel, so that the essential oil in the liquid conduit enters the connecting pipe in a bent flowing direction and sprays from the liquid outlet.

4. The aromatherapy nebulizer of claim 3, wherein the end of the connecting pipe is blocked via a sealing plug; the atomization chamber has a bottom wall, the liquid conduit is arranged vertically with a top end thereof passing through the bottom wall;
the connecting pipe is arranged horizontally on the bottom wall of the atomization chamber, and is connected to the liquid conduit to form the bent section of the essential oil channel that is bent from the top end of the liquid conduit, whereby the essential oil channel in the liquid conduit is bent from a vertical direction to a horizontal direction to spray the essential oil horizontally; or,
the connecting pipe is inclined at a predetermined angle with respect to the bottom wall, whereby the essential oil channel is bent into an inclined direction at the top end of liquid conduit and spray essential oil in an inclined direction.

5. The aromatherapy nebulizer of claim 4, wherein the liquid conduit, the air conduit, the connecting pipe, and the atomizing seat are a whole structure formed via a plastic molding process;
one end of the connecting pipe goes through a side wall of the atomizer, and is blocked via the sealing plug.

6. The aromatherapy nebulizer of claim 1, wherein the top end of the connecting pipe is blocked via a sealing plug;
said another channel is parallel to the liquid conduit or is set at a preset angle with respect to the liquid conduit, whereby, the essential channel is bent backwards parallel or obliquely from the top end of the liquid conduit;
the liquid conduit, the air conduit, the connecting pipe, and the atomizing seat are a whole structure formed via a plastic molding process.

7. The aromatherapy nebulizer of claim 1, wherein the atomizer further comprises one connecting pipe, one end of the connecting pipe is blocked, the other end is connected to the air conduit and forms the air outlet, whereby an air passage is bent from the air conduit to the connecting pipe to change a blowing direction of compressed air from the air outlet.

8. The aromatherapy nebulizer of claim 7, wherein the air conduit is arranged horizontally or at an inclined angel with respective to a bottom wall of the atomization chamber, and the connecting pipe is vertically arranged, whereby a horizontal or inclined air passage is bent vertically downwards to form the air outlet;
  the liquid conduit is connected to one horizontal or inclined connecting pipe of which one end is blocked, and the other end is connected to a top end of the liquid conduit and forms a liquid outlet, whereby the essential oil channel of the liquid conduit is bent into a horizontal or inclined section from the top of the liquid conduit, and the essential oil is sprayed in a horizontal or inclined direction;
  the liquid outlet is located below the air outlet;
  the liquid conduit, the air conduit, the connecting pipes, and the atomizing seat are a whole structure formed via a plastic molding process.

9. The aromatherapy nebulizer of claim 1, wherein a bottom surface of the outer cover is provided with a guiding channel, which is used to guide mist of atomized essential oil in the atomization chamber to the outlet to spay out, and is also used to condense droplets of the essential oil in the mist to filter and recycle droplets of the essential oil in the mist.

10. The aromatherapy nebulizer of claim 9, wherein the bottom surface of the outer cover is fitted with an inner cover to form a cavity therein; the guiding channel is in the cavity and between the outer cover and the inner cover; the inner cover is provided with a through hole which is used for the mist in the atomization chamber to enter the cavity, and is used for droplets of the essential oil to flow back to the atomization chamber.

11. An aromatherapy nebulizer, comprising an atomizer and an essential oil contained; wherein the atomizer is mounted on the essential oil container; the atomizer comprises an atomizing seat and an outer cover; an atomization chamber is formed in the atomizing seat, and a mist outlet is defined in the outer cover for communicating the atomization chamber with external environment the atomizing seat is provided with an air conduit and a liquid conduit the liquid conduit defines an essential oil channel therethrough for introducing the essential oil from the essential oil container into the atomization chamber; the air conduit defines an air passage therethrough for introducing compressed air into the atomization chamber to atomize the essential oil and has an air outlet in the atomization chamber; the essential oil channel is bent at one end of the liquid conduit which forms a liquid outlet in the atomization chamber, whereby the essential oil is absorbed upwards in the liquid conduct from the essential oil container and changes a direction sprayed out from the liquid outlet the air outlet and the liquid outlet corporate with each other so that the air conduit blows compressed air from the air outlet towards the liquid outlet and atomizes the essential oil;
  a bottom surface of the outer cover is provided with a guiding channel, which is used to guide mist of atomized essential oil in the atomization chamber to the outlet to spay out, and is also used to condense droplets of the essential oil in the mist to filter and recycle droplets of the essential oil in the mist;
  the bottom surface of the outer cover is fitted with an inner cover to form a cavity therein; the guiding channel is in the cavity and between the outer cover and the inner cover; the inner cover is provided with a through hole which is used for the mist in the atomization chamber to enter the cavity, and is used for droplets of the essential oil to flow back to the atomization chamber;
  a bottom wall of the atomization chamber is provided with a through hole communicated with the essential oil container so that the droplets of the essential oil in the atomization chamber flow back to the essential oil container;
  a bottom of the inner cover is fitted with a top of the air conduit or liquid conduit via a support structure.

12. The aromatherapy nebulizer of claim 1, wherein an annular groove is formed on an outer wall of the atomizing seat; or the atomizing seat is sleeved with an outer shell, an annular groove is formed on an outer wall of the outer shell;
  one end of the air guide pipe passes through a side wall of the atomizing seat to form an air inlet in the annular groove; when the atomizer is installed to a main body of an aroma diffuser, the annular groove is closed to form an annular air chamber, and the annular air chamber connects in air flowing an air pump in the aroma diffuser with the air inlet of the air conduit.

13. The aromatherapy nebulizer of claim 12, wherein an upper end and a lower end of the annular groove on the outer wall of the atomizing seat or the outer shell are respectively provided with a sealing ring for sealing annular air chamber.

14. An aroma diffuser, comprising:
  an aromatherapy nebulizer; and
  a main body, comprising:
  a control circuit board;
  a battery;
  buttons; and
  an air pump electrically connected with the battery and the control circuit board, and used for generating compressed air for the aromatherapy nebulizer to atomizing essential oil;
  the aromatherapy nebulizer comprising:
  an atomizer; and
  an essential oil container;
  the atomizer comprising:
  an atomizing seat defined an atomization chamber therein; and
  an outer cover defining a mist outlet which is used to spray mist of atomized essential oil in the atomization chamber to external environment;
  wherein the atomizing seat is provided with an air conduit and a liquid conduit; the liquid conduit defines an essential oil channel therethrough for introducing the essential oil from the essential oil container into the atomization chamber; the air conduit defines an air passage therethrough for introducing compressed air into the atomization chamber to atomize the essential oil and has an air outlet in the atomization chamber; the essential oil channel is bent at one end of the liquid conduit which forms a liquid outlet, whereby the essential oil is absorbed upwards to the liquid conduct from the essential oil container and changes a direction sprayed out from the liquid outlet; the air outlet and the liquid outlet corporate with each other so that the air outlet blows compressed air towards the liquid outlet;
  wherein a bent section of the essential oil channel is:
  bent into a return channel section to spray essential oil backwards;
  the atomizer further comprises one connecting pipe of which one end is blocked, and the other end is connected to the liquid conduit to form the bent section of the essential oil channel, so that the essential oil in the liquid conduit enters the connecting pipe in a bent flowing direction and sprays from the liquid outlet.

15. The aroma diffuser of claim 14, wherein the atomizer further comprises one connecting pipe, the connecting pipe is provided with a bottom wall therein, a top end of the connecting pipe is blocked and a cavity forms in the top end of the connecting pipe; a top end of the liquid conduit extends through the bottom wall to the cavity in the connecting pipe; the connecting pipe is provided with another channel therein of which a top end extending through the bottom wall to the cavity, whereby said another channel forms a bent section of the essential oil channel and connects the liquid conduit via the cavity of the connecting pipe.

16. The aroma diffuser of claim 14, wherein the atomizer further comprises one connecting pipe, one end of the connecting pipe is blocked, the other end is connected to the air conduit and forms the air outlet, whereby an air passage is bent from the air conduit to the connecting pipe to change a blowing direction of compressed air from the air outlet;

the air conduit is arranged horizontally or at an inclined angel with respective to a bottom wall of the atomization chamber, and the connecting pipe is vertically arranged, whereby a horizontal or inclined air passage is bent vertically downwards to form the air outlet;

the liquid conduit is connected to one horizontal or inclined connecting pipe of which one end is blocked, and the other end is connected to a top end of the liquid conduit and forms the liquid outlet, whereby the essential oil channel of the liquid conduit is bent into a horizontal or inclined section from the top of the liquid conduit, and the essential oil is sprayed in a horizontal or inclined direction;

the liquid outlet is located below the air outlet;

the liquid conduit, the air conduit, the connecting pipes, and the atomizing seat are a whole structure formed via a plastic molding process.

17. The aroma diffuser of claim 14, wherein a bottom surface of the outer cover is provided with a guiding channel, which is used to guide mist of atomized essential oil in the atomization chamber to the outlet to spay out, and is also used to condense droplets of the essential oil in the mist to filter and recycle droplets of the essential oil in the mist; a bottom surface of the outer cover is fitted with an inner cover to form a cavity therein; the guiding channel is in the cavity and between the outer cover and the inner cover; the inner cover is provided with a through hole which is used for the mist in the atomization chamber to enter the cavity, and is used for droplets of the essential oil to flow back to the atomization chamber.

18. The aroma diffuser of claim 14, wherein an annular groove is formed on an outer wall of the atomizing seat; or the atomizing seat is sleeved with an outer shell, an annular groove is formed on an outer wall of the outer shell;

one end of the air guide pipe passes through a side wall of the atomizing seat to form an air inlet in the annular groove; when the atomizer is installed to a main body of an aroma diffuser, the annular groove is closed to form an annular air chamber, and the annular air chamber connects in air flowing the air pump with the air inlet of the air conduit;

an upper end and a lower end of the annular groove on the outer wall of the atomizing seat or the outer shell are respectively provided with a sealing ring for sealing annular air chamber.

* * * * *